United States Patent
Pei

(10) Patent No.: US 8,233,980 B2
(45) Date of Patent: Jul. 31, 2012

(54) SYSTEM AND METHOD FOR DETECTING HIDDEN ATRIAL EVENTS FOR USE WITH AUTOMATIC MODE SWITCHING WITHIN AN IMPLANTABLE MEDICAL DEVICE

(75) Inventor: Xing Pei, Thousand Oaks, CA (US)

(73) Assignee: Pacesetter, Inc., Sylmar, CA (US)

(*) Notice: Subject to any disclaimer, the term of this patent is extended or adjusted under 35 U.S.C. 154(b) by 941 days.

(21) Appl. No.: 12/116,450

(22) Filed: May 7, 2008

(65) Prior Publication Data

US 2009/0281587 A1  Nov. 12, 2009

(51) Int. Cl.
*A61N 1/362* (2006.01)

(52) U.S. Cl. .......... 607/9; 607/11; 607/14; 607/17; 607/115; 607/116; 607/119; 607/123

(58) Field of Classification Search .......... 607/9, 11, 607/14, 17, 115–116, 119, 123
See application file for complete search history.

(56) References Cited

U.S. PATENT DOCUMENTS

| | | |
|---|---|---|
| 4,712,555 A | 12/1987 | Thornander et al. |
| 4,920,965 A | 5/1990 | Funke et al. |
| 4,940,052 A | 7/1990 | Mann et al. |
| 4,944,298 A | 7/1990 | Sholder |
| 5,269,299 A | 12/1993 | Duncan |
| 5,400,796 A | 3/1995 | Wecke |
| 5,441,523 A | 8/1995 | Nappholz |
| 5,466,254 A | 11/1995 | Helland |
| 5,476,483 A | 12/1995 | Bornzin et al. |
| 5,584,867 A | 12/1996 | Limousin et al. |
| 5,591,214 A | 1/1997 | Lu |
| 5,653,738 A | 8/1997 | Sholder |
| 5,778,881 A | 7/1998 | Sun et al. |
| 6,459,928 B2 | 10/2002 | Mika et al. |
| 6,477,416 B1 | 11/2002 | Florio et al. |
| 6,553,258 B2 | 4/2003 | Stahmann et al. |
| 6,564,097 B1 | 5/2003 | Williams et al. |
| 6,625,490 B1 | 9/2003 | McClure et al. |
| 6,650,931 B1 | 11/2003 | McClure et al. |
| 6,934,585 B1 | 8/2005 | Schloss et al. |
| 2003/0097157 A1 | 5/2003 | Wohlgemuth et al. |

OTHER PUBLICATIONS

Barold, S. Serge MD et al.,"Complex Manifestations of an Automatic Mode Switching Algorithm," PACE. Jan. 2007:30:112-114.
Kawanishi, David et al., "Closer investigation of oversensing: sense amplifier signal analysis," Europace 2001. 2 (Supp B):B146—Abstract 454.
Queiroga, Andre et al., "Overdrive pacing for atrial fibrillation—complications and ways to overcome them," Europace 2001;2(Supp B):B203—Abstract 648.
NonFinal Office Action, mailed Oct. 10, 2006: Related U.S. Appl. No. 10/979,833.
Final Office Action, mailed Jul. 13, 2007: Related U.S. Appl. No. 10/979,833.

*Primary Examiner* — Carl H Layno
*Assistant Examiner* — Deborah Malamud

(57) ABSTRACT

Techniques are provided for detecting atrial events that might be hidden due to the operation of a post-ventricular atrial blanking (PVAB) interval or other atrial channel blanking interval. In one example, candidate atrial events are identified within signals occurring during the PVAB interval. Then, a determination is made as to whether the candidate atrial event is a true atrial event based on a comparison of characteristics of the candidate atrial event with characteristics of prior known atrial events within the patient. By comparing the characteristics of the "hidden" event with the characteristics of prior known atrial events within the patient, a quick and accurate determination can be made whether the event should be counted as a P-wave. In this manner, hidden atrial arrhythmias can be detected and mode switch oscillations can be reduced or eliminated.

15 Claims, 13 Drawing Sheets

FIG. 1-1

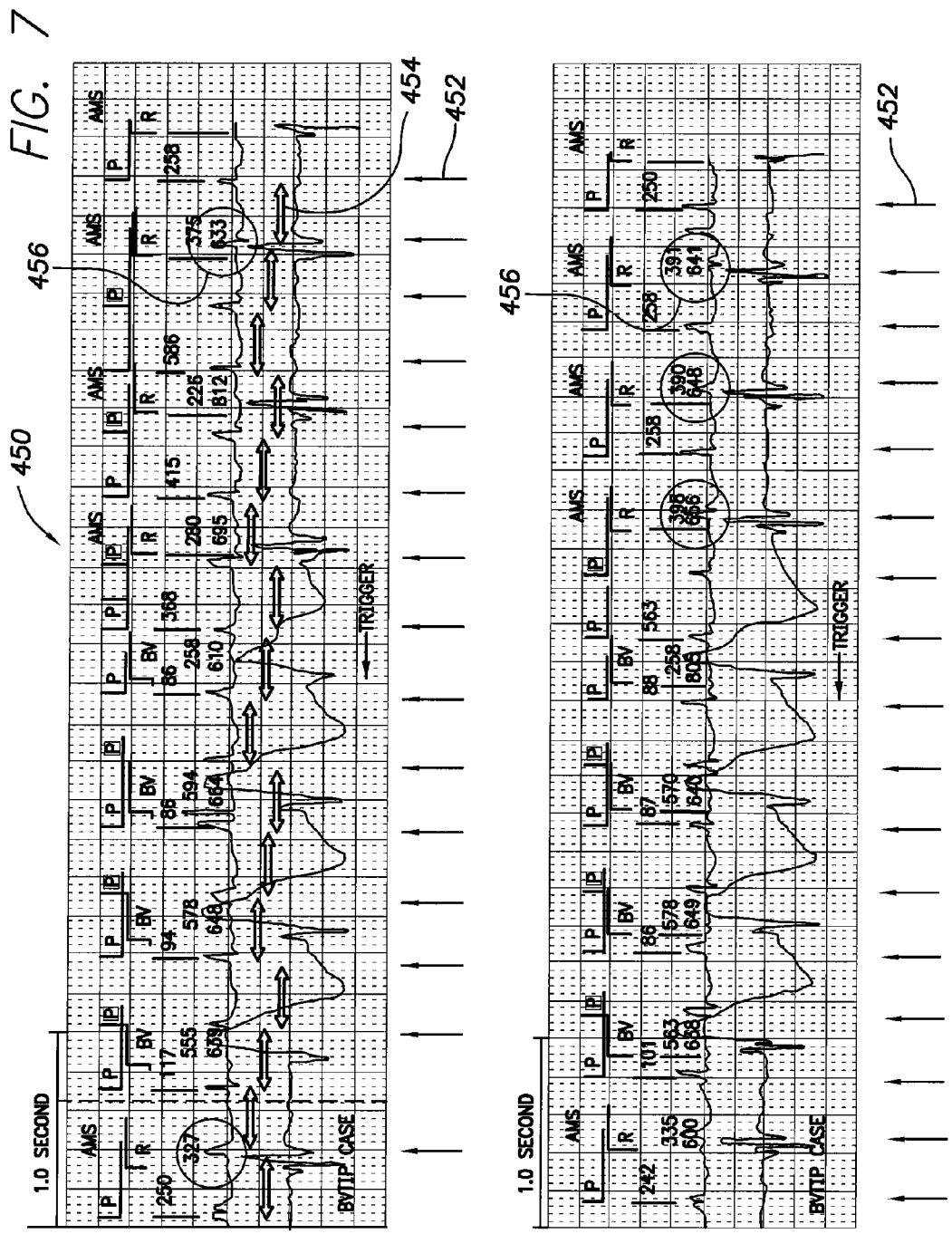

SYSTEM AND METHOD FOR DETECTING HIDDEN ATRIAL EVENTS FOR USE WITH AUTOMATIC MODE SWITCHING WITHIN AN IMPLANTABLE MEDICAL DEVICE

FIELD OF THE INVENTION

The invention relates generally to implantable cardiac stimulation devices, such as pacemakers and implantable cardioverter/defibrillators (ICDs), and in particular to techniques for detecting hidden atrial events for use in improving automatic mode switching (AMS) within such devices, as well as improving the detection of atrial arrhythmias.

BACKGROUND OF THE INVENTION

Pacemakers and ICDs carefully monitor characteristics of the heart, such as the heart rate, to detect arrhythmias, discriminate among different types of arrhythmias, identify appropriate therapy, and determine when to administer the therapy. The device tracks the heart rate by examining electrical signals that result in the contraction and expansion of the chambers of the heart. The contraction of atrial muscle tissue is triggered by the electrical depolarization of the atria, which is manifest as a P-wave in a surface electrocardiogram (ECG) and as a rapid deflection (intrinsic deflection) in an intracardiac electrogram (IEGM). The contraction of ventricular muscle tissue is triggered by the depolarization of the ventricles, which is manifest on the surface ECG by an R-wave (also referred to as the "QRS complex") and as a large rapid deflection (intrinsic deflection) within the IEGM. Repolarization of the ventricles is manifest as a T-wave in the surface ECG and a corresponding deflection in the IEGM. A similar depolarization of the atrial tissue usually does not result in a detectable signal within either the surface ECG or the IEGM because it is usually small, coincides with, and is obscured by the R-wave. Note that, although the terms P-wave, R-wave and T-wave often refer to features of the surface ECG, herein the terms are used to also refer to the corresponding signals sensed internally. Also, where an electrical signal is generated in one chamber but sensed in another, it is referred to herein, where needed, as a "far-field" signal. Hence, an R-wave sensed in the atria is referred to as a far-field R-wave.

The sequence of electrical events that represent P-waves, followed by R-waves (or QRS complexes), followed by T-waves can be detected within IEGM signals sensed using pacing leads implanted inside the heart. To help prevent misidentification of electrical events and to more accurately detect the heart rate, the stimulation device employs one or more refractory periods and blanking periods. Within a refractory period, the device does not process electrical signals during a predetermined interval of time—either for all device functions (an absolute refractory period) or for selected device functions (a relative refractory period). That is, the signals in the refractor period are discarded. As an example of a refractory period, upon detection of an R-wave on a ventricular sensing channel (or upon delivery of a V-pulse to the ventricles), a Post-Ventricular Atrial Refractory Period (PVARP) is initiated on an atrial sensing channel. A first portion of the PVARP comprises a post ventricular atrial blanking (PVAB) interval wherein the pacemaker can detect signals on the atrial channel but does not use the signals for any purpose. The PVAB interval is provided to prevent the device from erroneously responding to far-field ventricular events (such as far-field R-waves or far-field ventricular evoked responses (VERs)) on the atrial channel. The PVARP concludes with a relative refractory period during which the pacemaker continues to ignore all signals detected on the atrial channel as far as the triggering or inhibiting of pacing functions is concerned, but not for other functions, such as detecting rapid atrial rates or recording diagnostic information.

Accurate detection of heart rates is required, for example, for the purposes of enabling an AMS system wherein the pacemaker switches from a tracking mode such as DDD to a non-tracking mode such as VDI or DDI mode. More specifically, the conventional pacemaker typically compares a current atrial rate with an atrial tachycardia detection threshold (ATDR) and, if it exceeds the threshold, atrial tachycardia is assumed and the pacemaker switches from the tracking mode to the non-tracking mode. Details regarding AMS may be found in the following patents: U.S. Pat. Nos. 5,441,523 and 5,591,214. Note that DDD, VDI, VVI and DDI are standard device codes that identify the mode of operation of the device. DDD indicates a device that senses and paces in both the atria and the ventricles and is capable of both triggering and inhibiting functions based upon events sensed in the atria and the ventricles. VVI indicates that the device is capable of pacing and sensing only in the ventricles but is only capable of inhibiting the functions based upon events sensed in the ventricles. VDI is identical to VVI except that it is also capable of sensing intrinsic atrial activity. DDI is identical to DDD except that the device is only capable of inhibiting functions based upon sensed events, rather than triggering functions. As such, the DDI mode is a non-tracking mode precluding it from triggering ventricular outputs in response to sensed atrial events. Numerous other device modes of operation are possible, each represented by standard abbreviations of this type.

Thus, an AMS system recognizes when the patient is in an atrial arrhythmia such as atrial tachycardia (AT) and/or atrial fibrillation (AF) and switches from the tracking mode to the non-tracking mode to prevent the device from attempting to track the high atrial rates associated with AT/AF. Problems, however, can arise if some rapid atrial events (arising, e.g., due to atrial flutter or AT/AF) occur during the PVAB interval and hence are not detected by the device, or are only intermittently detected. Due to such "hidden" atrial events, the AMS system can potentially switch back and forth between tracking and non-tracking modes, a condition referred to as "mode switch oscillation." The result is that the patient is alternately paced at a higher ventricular rate (when in the tracking mode) and at a much lower ventricular rate (when in the non-tracking mode), which is unpleasant for the patient and can also increase patient morbidity. Mode switch oscillation can also yield inappropriate diagnostic data that might mislead tiered atrial arrhythmia therapy systems, such as atrial burst-pacing systems, to falsely conclude that therapy is effective, even if ineffective.

FIG. 1 illustrates mode switch oscillation by way of six stored IEGMs collected by a pacemaker implanted within a patient. The IEGM graphs 2 were recorded over a period of about eighty-seconds. The pacemaker was initially in the DDD mode. The starting time for each individual IEGM graph is shown at the beginning of the traces. (Note, however, that within each individual IEGM graph, only the first six seconds of data for that particular interval is shown. Hence, the entire eighty seconds of IEGM data is not completely illustrated.) Each IEGM graphs includes two traces—an atrial trace recorded in a bipolar sensing configuration (A-tip to A-ring) and a ventricular trace in a unipolar sensing configuration (V-tip to case), as well as various event markers identifying P-waves, R-waves, etc. In particular, "trigger" event codes indicate when a mode switch to a non-tracking mode was triggered due to a high detected atrial rate. For clarity in the figure, the mode switching events are further identified by vertical phantom lines 4 followed by "NON-TRACKING" labels. Following each mode switch to the non-tracking mode, individual AMS event codes 6 are applied to individual beats that are "non-tracked." (Note that it starts marking the first non-tracking ventricular event after the initial trigger to the first "AMS" beat.) Mode switching events back to the tracking mode are identified by way of vertical phantom lines 8 followed by "TRACKING" labels.

Collectively, the IEGM graphs indicate that the pacemaker went through six mode switch operations from the tracking mode to the non-tracking mode during the overall period of about eighty seconds, with the shortest interval between automatic mode switches being only about eight seconds. A close look at the IEGM traces reveals that the patient experienced AT throughout the entire eighty second interval. However, many of the atrial events (i.e. P-waves) occurred during PVAB intervals and, as such, were not detected by the device for the purposes of atrial rate calculation. These hidden events are marked by circles, such as those identified by reference numeral 9. Since the atrial events were hidden within the PVAB interval, the events were not used in the atrial rate calculations, resulting in significant variations in the calculated atrial rate. The variations caused the device to switch back and forth between the tracking mode and the non-tracking mode, i.e. the aforementioned mode switch oscillation occurred. As such, the underlying atrial arrhythmia was frequently hidden during the non-tracking operating mode due to the PVAB interval.

The PVAB interval is important for managing the potential oversensing of ventricular events on the atrial channel. However, as illustrated in FIG. 1, the PVAB interval can result in inappropriate mode switching, including frequent mode switch oscillations. Accordingly, it would be desirable to provide improved techniques for avoiding inappropriate mode switching, particularly due to hidden atrial arrhythmias, and it is to this end that the invention is primarily directed. Such improved techniques help reduce discomfort and risk to the patient and generally improve the quality of life of the patients.

SUMMARY OF THE INVENTION

In an exemplary embodiment of the invention, techniques are provided for detecting and identifying atrial events during blanking intervals to, for example, avoid mode switch oscillations within implantable medical devices equipped to perform AMS. In one example, a post-ventricular event interval, such as a PVAB interval, is tracked within electrical cardiac signals sensed by the device. A candidate atrial event is identified within the signals occurring during the post-ventricular event interval and then a determination is made as to whether the candidate atrial event is a true atrial event based on a comparison of characteristics of the candidate atrial event and characteristics of prior atrial events within the patient. For example, when a possible "hidden" atrial event is identified within a PVAB interval, the event is compared with previous known P-waves within the patient to determine whether the event is an actual P-wave and, if so, it is then used in atrial rate calculations. Otherwise, it is rejected. By comparing the "hidden" event with known P-waves within the patient, a quick and accurate determination can be made as to whether the event should counted as a P-wave for atrial rate calculations or for other purposes. In this manner, hidden atrial arrhythmias can be detected and mode switch oscillations can be reduced or eliminated.

In one particular example, the implantable device continually tracks P-waves and attempts to predict when the next P-wave will occur. If the next P-wave is expected to occur during a PVAB interval, the device searches inside the PVAB interval for hidden events. For example, the device may compare atrial channel signals sensed within the PVAB interval against a predetermined sensing threshold to detect candidate events. The device then determines whether the candidate event is a true atrial event based on one or more of: prior atrial event intervals, prior atrial event patterns and prior atrial event morphology. In one example, the device determines whether the timing of the event corresponds to an ongoing atrial pattern, such as a pattern of uniform atrial intervals, lengthening atrial intervals, shortening atrial intervals, or alternating atrial intervals. If the timing of the candidate event corresponds to the on-going atrial pattern, the device then compares the morphology of the event to the morphology of prior atrial events within the patient to confirm the event as a true P-wave. In some implementations, the device performs an additional confirmation procedure based on the alteration of pacing intervals. That is, the device changes the current pacing interval so that the predicted timing for the next atrial event likewise changes. Then the device determines whether additional hidden events occur with the new predicting timing and, if so, the events are confirmed as true atrial events. If not, the events are rejected.

Preferably, all true atrial events are used in atrial rate calculations for the purposes of controlling device operations, including mode switching and the activation of atrial tachycardia suppression therapy, such as anti-tachycardia pacing (ATP) therapy.

Thus, techniques are provided for detecting hidden atrial events and arrhythmias and for avoiding inappropriate mode switching within pacemakers or other implantable cardiac rhythm management devices. Other objects, features and advantages of the invention will be apparent from the detailed description to follow.

BRIEF DESCRIPTION OF THE DRAWINGS

The above and further features, advantages and benefits of the invention will be apparent upon consideration of the description taken in conjunction with the accompanying drawings, in which:

FIG. 7 includes graphs of patient IEGMs illustrating hidden atrial events processed by the techniques of FIGS. 3-6;

DETAILED DESCRIPTION OF THE PREFERRED EMBODIMENTS

The following description includes the best mode presently contemplated for practicing the invention. This description is not to be taken in a limiting sense but is made merely to describe general principles of the invention. The scope of the invention should be ascertained with reference to the issued claims. In the description of the invention that follows, like numerals or reference designators will be used to refer to like parts or elements throughout.

Overview of Implantable System

Figures 1, 2:
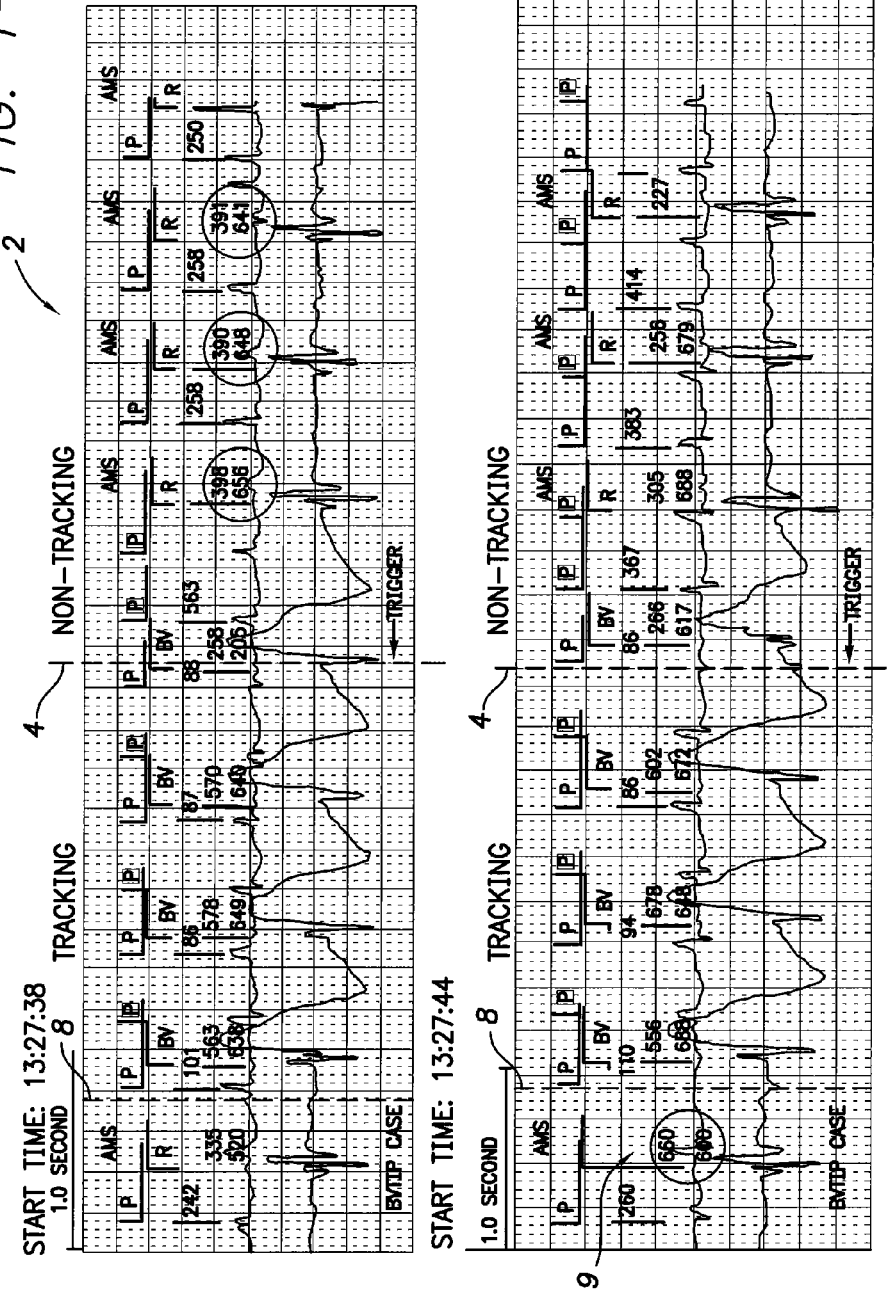
FIG. 1 includes graphs of patient IEGMs illustrating mode switching oscillations due to hidden atrial events.
FIG. 2 illustrates pertinent components of an implantable medical system having a pacer/ICD capable of detecting hidden atrial events and arrhythmias and for controlling AMS in response thereto.
Figure 8:
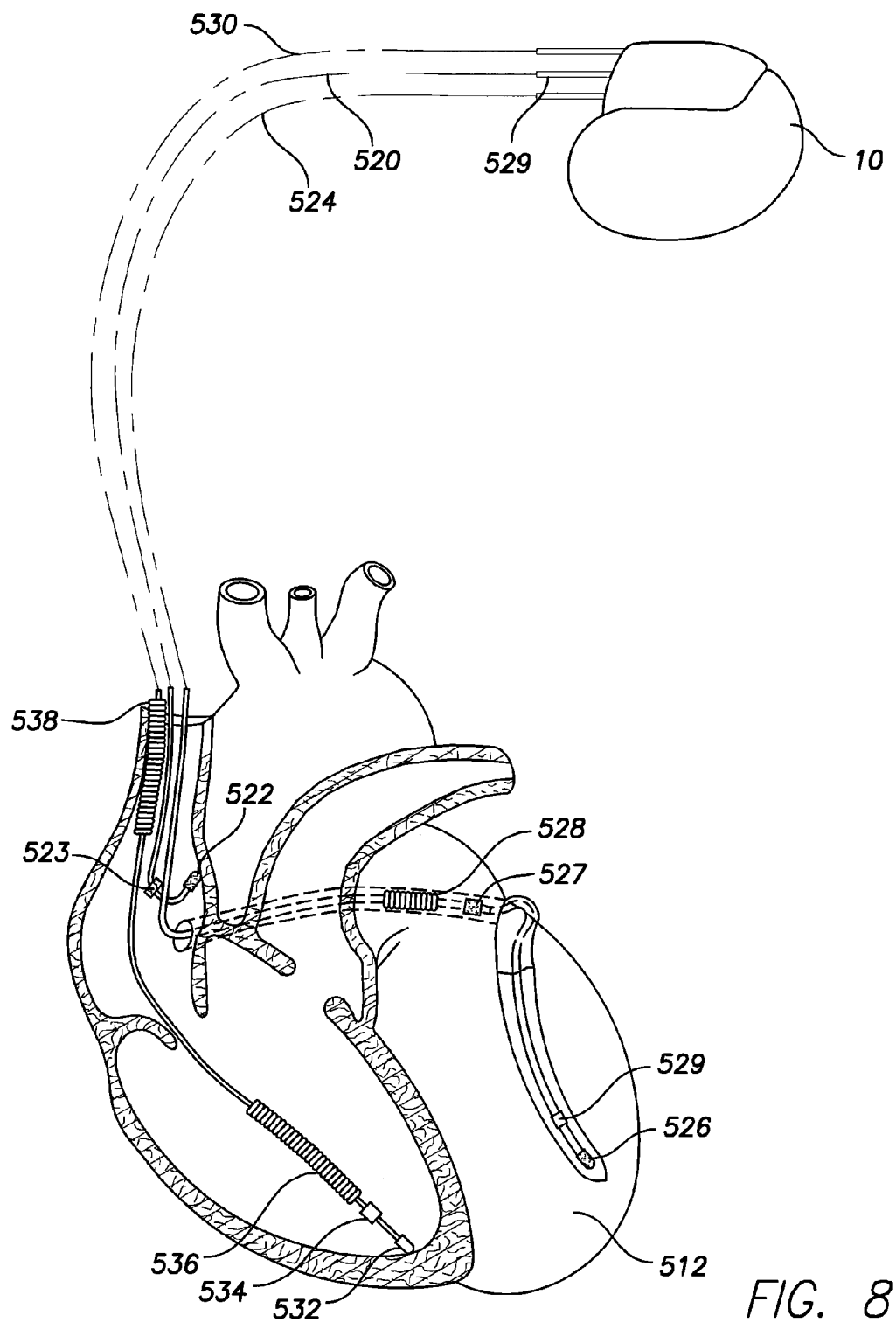
FIG. 8 is a simplified, partly cutaway view, illustrating the pacer/ICD of FIG. 2 along with a complete set of leads implanted in the heart of a patient.

FIG. 2 illustrates an implantable medical system 8 having a pacer/ICD 10 capable of detecting hidden atrial events and arrhythmias within the patient in which the pacer/ICD is implanted, based on electrical cardiac signals sensed during a PVAB interval or other atrial channel blanking interval. To sense electrical cardiac signals, the pacer/ICD uses a set of cardiac pacing/sensing leads 12 implanted on or within the heart of the patient from which one or more IEGM signals is derived. In FIG. 2, a stylized representation of the leads is provided. A more thorough and anatomically accurate illustration of the set of pacing leads is illustrated in FIG. 8, discussed below. Exemplary techniques used by the pacer/ICD to analyze cardiac signals sensed by the leads for use in enabling mode switching, detecting atrial arrhythmias, delivering therapy, and generating diagnostics data are described with reference to FIGS. 3-7. Therapy to be delivered in response to an atrial arrhythmia may include, e.g., cardioversion therapy in response to atrial fibrillation, or various forms of ATP in response to other atrial arrhythmias. The device may also be equipped to perform dynamic atrial overdrive (DAO) pacing to prevent the onset of atrial arrhythmias.

Diagnostic data generated by the pacer/ICD pertaining to atrial arrhythmias or other conditions within the patient may be transmitted using a short-range telemetry system to an external programmer 14 (or to other suitable devices such as a bedside monitor or a handheld diagnostics device, not separately shown) for review by a physician or other medical professional. The physician may then adjust the operation of the pacer/ICD to activate, deactivate or otherwise control any therapies that are automatically applied. Warning signals may also be sent to the external device to warn the patient or medical professionals of any condition the device itself is unable to remedy.

Hence, FIG. 2 provides an overview of an implantable system having components for detecting otherwise hidden atrial events/arrhythmias and for delivering appropriate therapy or warnings. Note that the particular locations, orientations and relative sizes of the implanted components shown in FIG. 2 are merely illustrative and may not necessarily correspond to actual implant locations, orientations or relative sizes.

Hidden Atrial Arrhythmia Detection Overview

Figures 1, 2, 3:
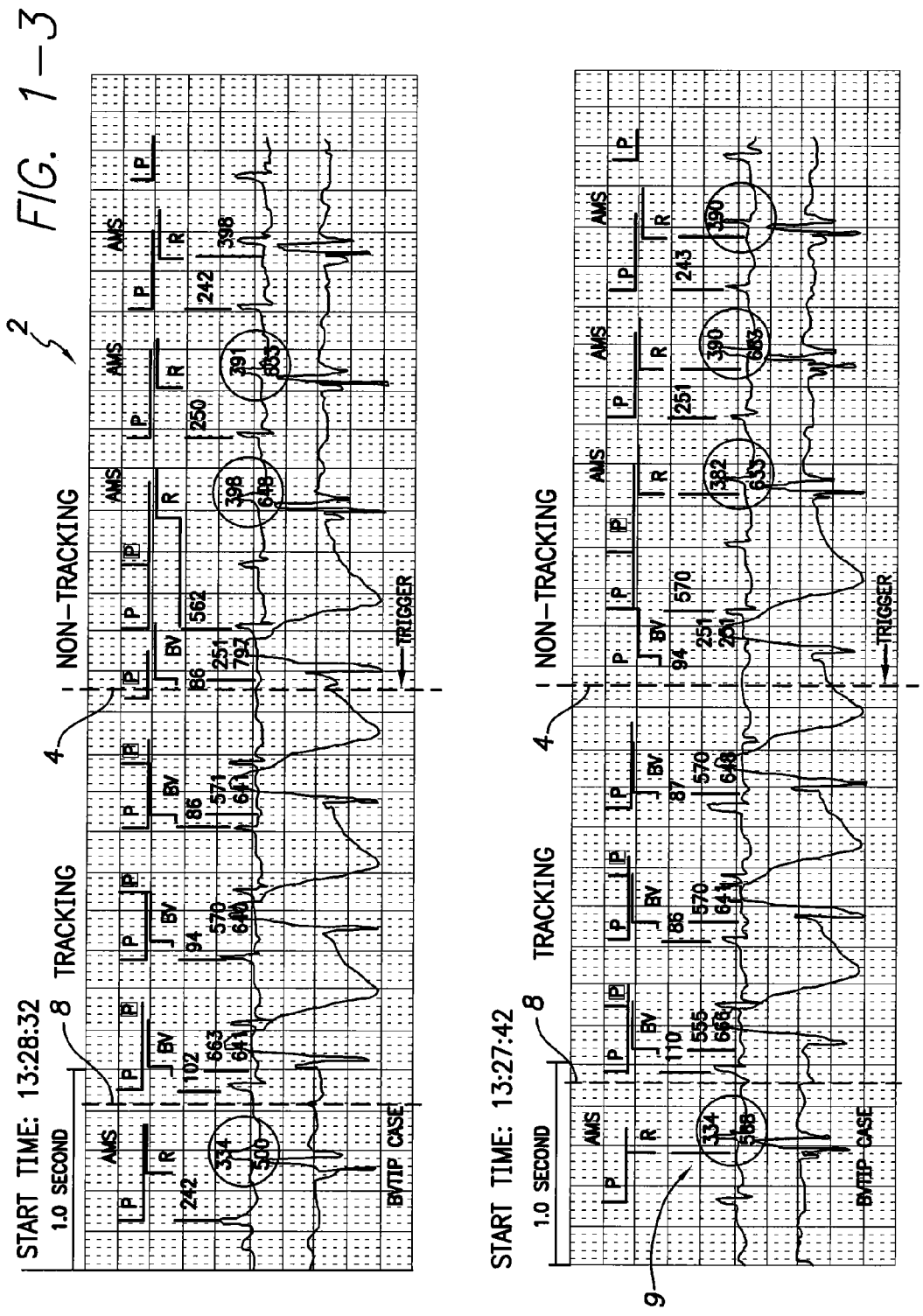
FIG. 3 is a flow chart summarizing a technique by which the pacer/ICD of FIG. 2 detects atrial events during post-ventricular blanking intervals for use in detecting hidden atrial arrhythmias and controlling mode switching.
Figure 2:
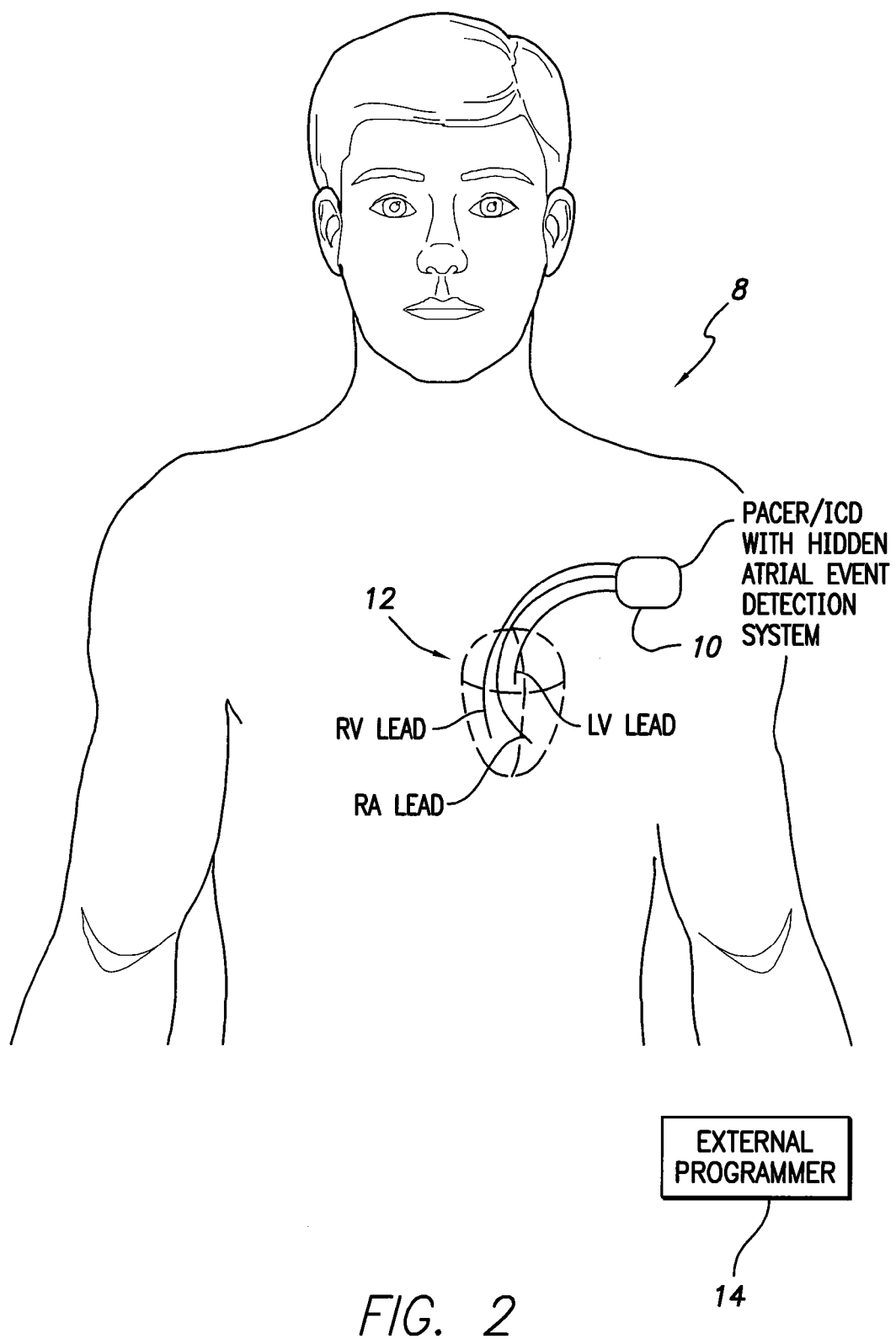
Figure 3:
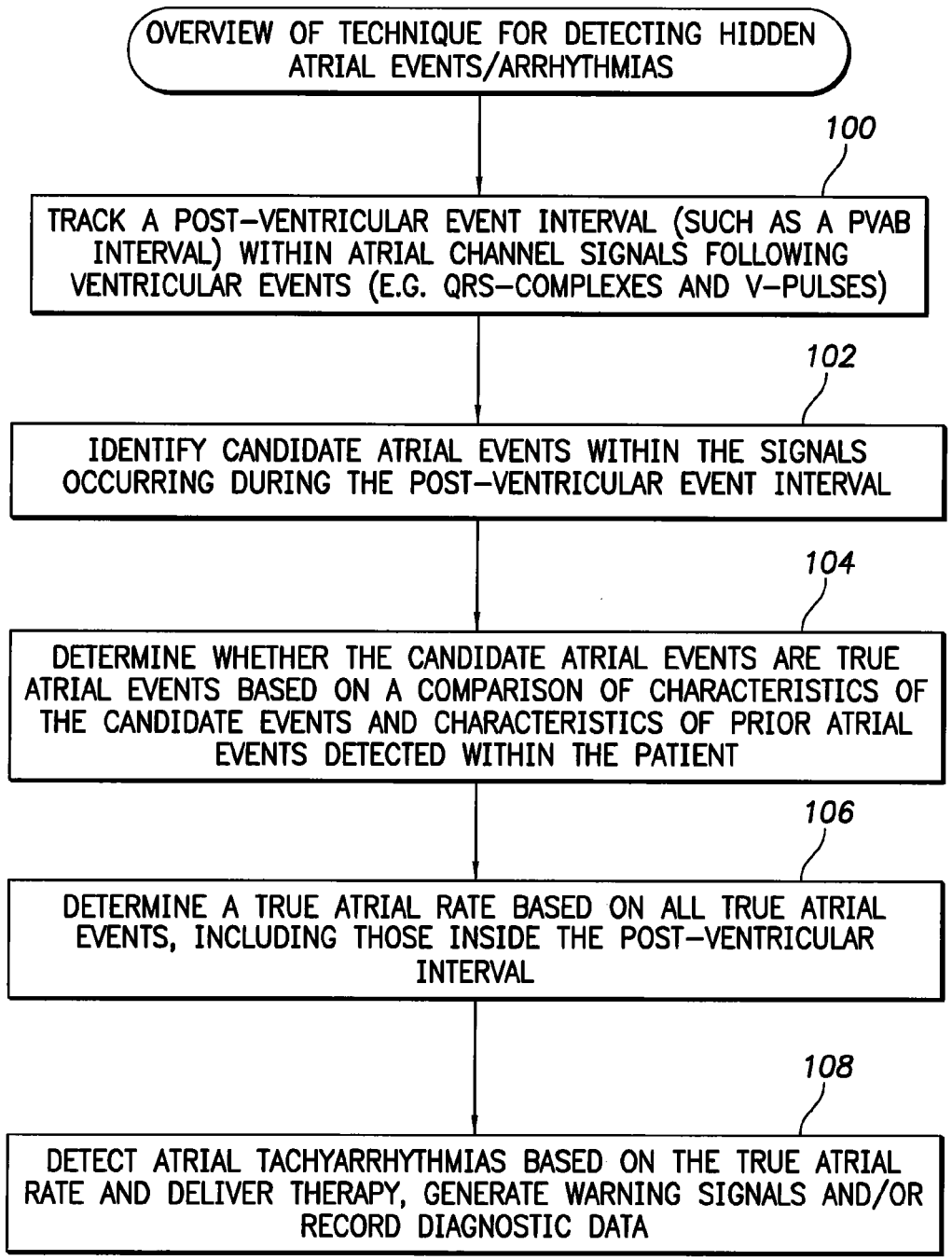

FIG. 3 broadly summarizes the hidden atrial event/arrhythmia detection technique performed by the system of FIG. 2. Briefly, at step 100, the pacer/ICD tracks a post-ventricular event interval within atrial channel signals following ventricular events. Typically, the post-ventricular event interval is a blanking interval (i.e. a PVAB interval), which is activated by the pacer/ICD following QRS-complexes (i.e. R-waves) and V-pulses. As discussed above, such blanking intervals are provided to prevent the pacer/ICD from inappropriately responding to far-field R-waves, far-field ventricular evoked responses (VERs) or other far-field ventricular events appearing on the atrial channel. At step 102, the pacer/ICD identifies candidate atrial events (i.e. P-waves) within the signals occurring during the post-ventricular event interval. That is, the pacer/ICD identifies electrical events within the atrial channel signal during the PVAB interval that might be hidden P-waves or which might instead be far-field R-waves or far-field VERs. Preferably, the magnitude of the atrial channel electrical signal within the PVAB interval is compared against a P-wave detection threshold. Any event exceeding the threshold is regarded as a candidate P-wave.

At step 104, the pacer/ICD determines whether the candidate atrial events (i.e. P-waves) are true atrial events, based on a comparison of characteristics of the candidate events and characteristics of prior atrial events detected within the patient. As will be explained further, such characteristics may include the timing of the event relative to other P-waves and/or the morphology of the event, and may further take into account various known patterns of P-waves. In any case, by comparing the characteristics of candidate P-waves with the characteristics of prior known P-waves within the patient, true P-waves can be readily distinguished from false P-waves (e.g. far-field R-waves or far-field VERs). At step 106, the pacer/ICD then determines a true atrial rate based on all true P-waves, including those inside the PVAB interval. In this manner, P-waves that might otherwise be hidden within the PVAB interval are detected and used to determine the atrial rate, thereby avoiding any significant under-estimation of the atrial rate, which may result in inappropriate mode switching, or the inappropriate delivery or inhibition of pacing pulses or other pacing therapy.

At step 108, the pacer/ICD then detects atrial tachyarrhythmias based on the true atrial rate and delivers therapy, generates warnings and/or records diagnostic data. By more accurately calculating the true atrial rate, atrial tachyarrhythmias are more reliably detected and therapy is more reliably controlled. In this manner, so-called hidden atrial arrhythmias are detected and addressed.

Illustrative Embodiment

Figures 1, 4:
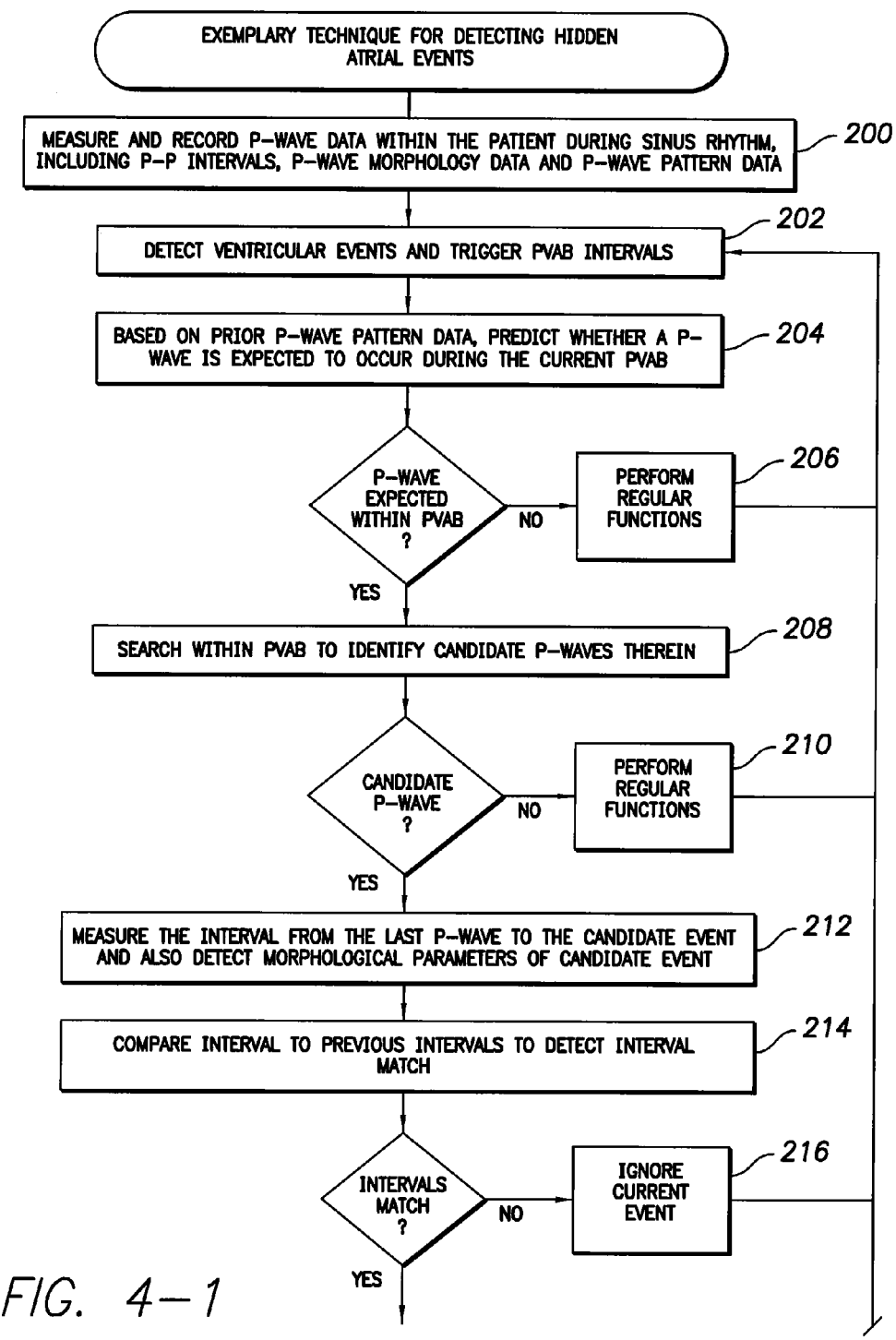
FIG. 4 illustrates an exemplary hidden atrial event detection technique performed in accordance with the general technique of FIG. 3.
Figures 2, 4:
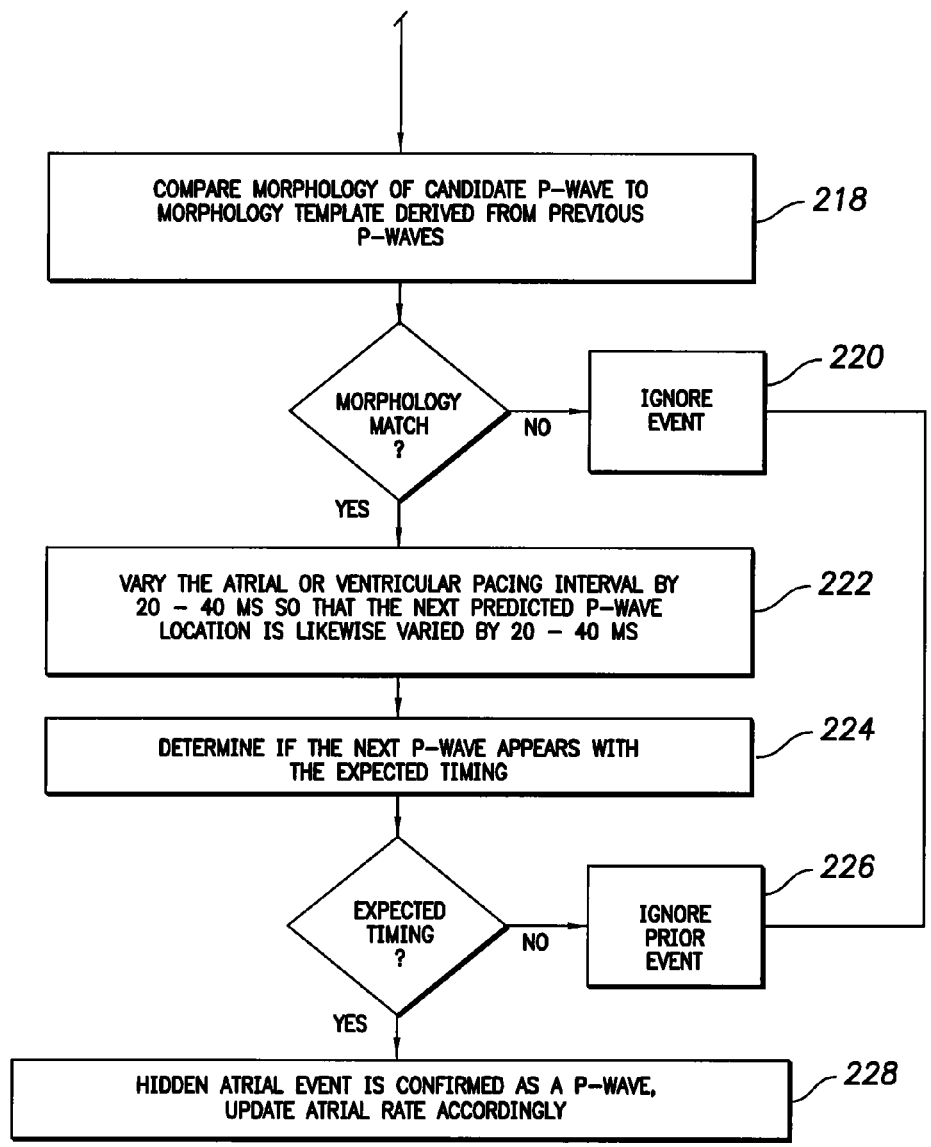

FIG. 4 illustrates, in greater detail, an exemplary atrial event detection technique performed in accordance with the general technique of FIG. 3. Beginning at step 200, during normal sinus rhythm, the pacer/ICD detects P-waves, then measures and records P-wave data within the patient, including P-P intervals (i.e. the intervals between each successive P-wave), P-wave morphology data and P-wave pattern data. The P-wave morphology data may be stored in the form of a template representative of the shape of the P-wave. Alternatively, individual morphological parameters may be stored separately, such as peak amplitude, width, etc. Insofar as P-wave patterns are concerned, the pacer/ICD examines the intervals between P-waves to detect any ongoing patterns such as patterns indicative of uniform intervals, gradually lengthening intervals, gradually shortening intervals, and alternating intervals (such as patterns arising due to bigeminy, trigeminy, etc.) Otherwise conventional pattern recognition techniques can be exploited.

At step 202, the pacer/ICD detects ventricular events (i.e. R-waves and delivery of V-pulses) and triggers PVAB intervals, in accordance with otherwise conventional techniques. At step 204, the pacer/ICD predicts, based on prior P-wave pattern data, whether a P-wave is expected to occur during the current PVAB interval. That is, the pacer/ICD uses the timing of the latest P-wave along with the most recent P-P intervals and information specifying any on-going P-wave patterns, and predicts the likely timing of the next P-wave. As each new PVAB interval is triggered, the pacer/ICD can thereby determine whether the predicted timing of next P-wave will place the P-wave within the PVAB interval. If not, then at step 206, the device performs its regular functions (and hence the current PVAB interval is not used for the purposes of detecting hidden P-waves.) If, however, a P-wave is expected to occur during the PVAB interval, then at step 208, the pacer/ICD searches within the PVAB interval to identify any candidate P-waves therein, i.e. the device opens a search window within the PVAB interval to examine atrial IEGM signals that would otherwise be completely ignored by the device. If, contrary to the prediction, no event is found during the current PVAB interval (or during a selected portion of the PVAB interval centered on the expected location of the P-wave), the device performs its regular functions, at step 210. If, however, an event is detected within the PVAB interval, then the event is classified as a candidate P-wave.

Assuming a candidate P-wave has been found then, at step 212, the pacer/ICD measures the interval from the last known P-wave to the candidate event (i.e. the new P-P interval) and also detects morphological parameters of the candidate event, such as its amplitude, width, slew rate, etc. At step 214, the pacer/ICD then compares the measured interval to previous P-P intervals to determine whether there is a match. The comparison preferably takes into account any on-going P-wave interval patterns, such as lengthening patterns, shortening patterns, alternating patterns, etc. If the new P-P interval is inconsistent with prior intervals, then the candidate event is ignored, at step 216. In that case, the event is probably a far-field R-wave, T-wave or VER. Assuming, however, that the new P-P interval is substantially consistent with prior intervals (within acceptable predetermined comparison ranges), the candidate P-wave is deemed to be a true P-wave. In some implementations, at this point, the P-wave is immediately counted for the purposes of atrial rate calculations. In the example of FIG. 4, however, further processing is employed to confirm that the P-wave is a true P-wave before it is counted.

At step 218, to confirm the P-wave, the pacer/ICD compares the morphology of the candidate P-wave to the morphology template derived from previous known P-waves (and stored at step 200). In some examples, the device compares the shape of the new P-wave against the pre-stored template. In other examples, the device merely compares one or two particular morphological parameters, such as amplitude, width, etc., against the corresponding parameters of the template. In any case, if there is no match, the P-wave is rejected, at step 220, as being a false P-wave (most likely a far-field ventricular event that coincidentally appeared at the predicted location of a hidden P-wave.) Then, at step 222, the pacer/ICD varies the atrial or ventricular pacing interval by 20-40 milliseconds (ms) so that the next predicted P-wave location is likewise varied by 20-40 ms. At step 224, the pacer/ICD then determines if the next P-wave appears with the expected timing (i.e. whether the timing of the next P-wave is likewise shifted by the adjusted amount, as expected.) If the next P-wave does not occur at the expected, shifted timing, the hidden P-wave initially detected with the PVAB interval (back at step 208) is ignored, at step 226, as being a false P-wave. Otherwise, the hidden P-wave is confirmed, at step 228, as a true P-wave, and the atrial rate is updated accordingly. Typically, steps 222-224 are performed only if there is a series of hidden P-waves. Although not shown in FIG. 4, the pacer/ICD then controls AMS, detects atrial arrhythmias, etc., as already explained.

Thus, FIG. 4 illustrates an exemplary implementation wherein a variety of tests are performed to detect hidden P-waves and to confirm the hidden P-waves as true P-waves. The steps need not be performed in the order shown. For example, rather than examining morphology before altering the atrial or ventricular pacing intervals, as shown, the device could instead alter pacing intervals as a first confirmation step, before examining P-wave morphology. Also, not all confirmation steps need be performed. In some implementations, the alteration in pacing intervals is performed to confirm the P-wave, but no morphological analysis is performed, or vice versa. As can be appreciated, a variety of individual procedures may be performed in accordance with the general principles of the invention.

Detailed Example

Figure 5:
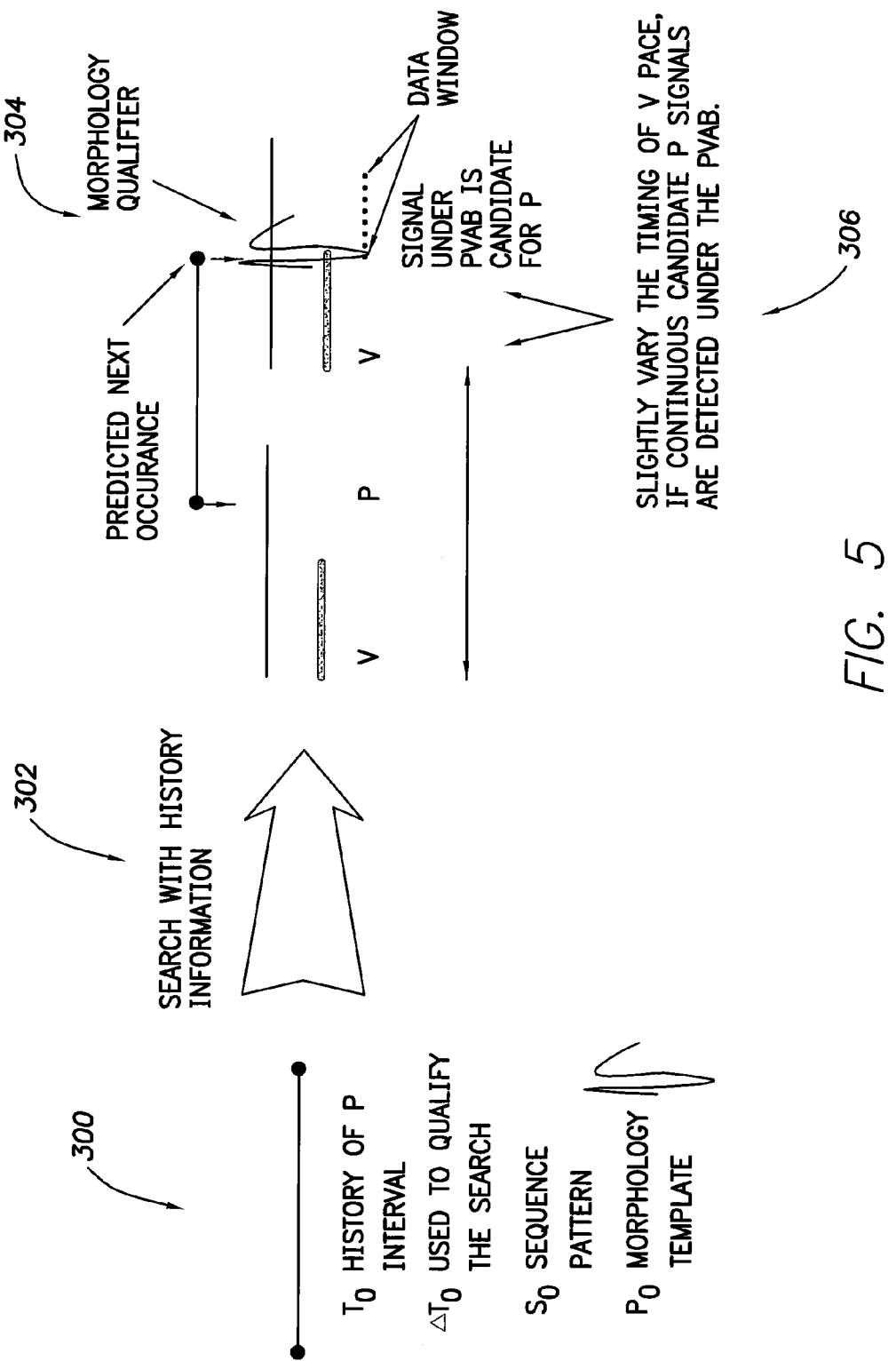
FIG. 5 graphically illustrates another exemplary technique in accordance with the general technique of FIG. 3.
Figures 1, 6:
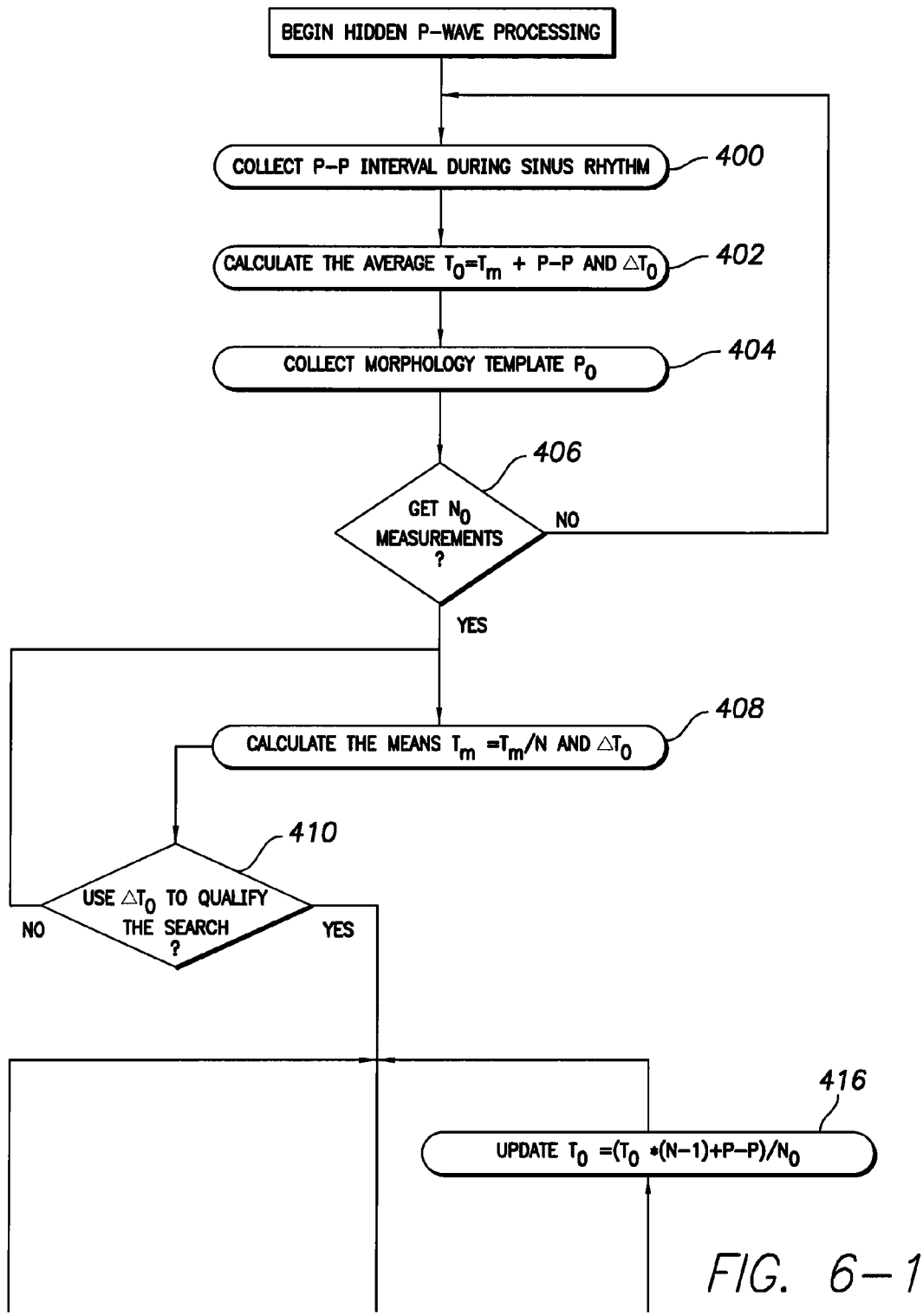
FIG. 6 is a flow chart that illustrates, in greater detail, the exemplary technique of FIG. 5.
Figures 2, 6:
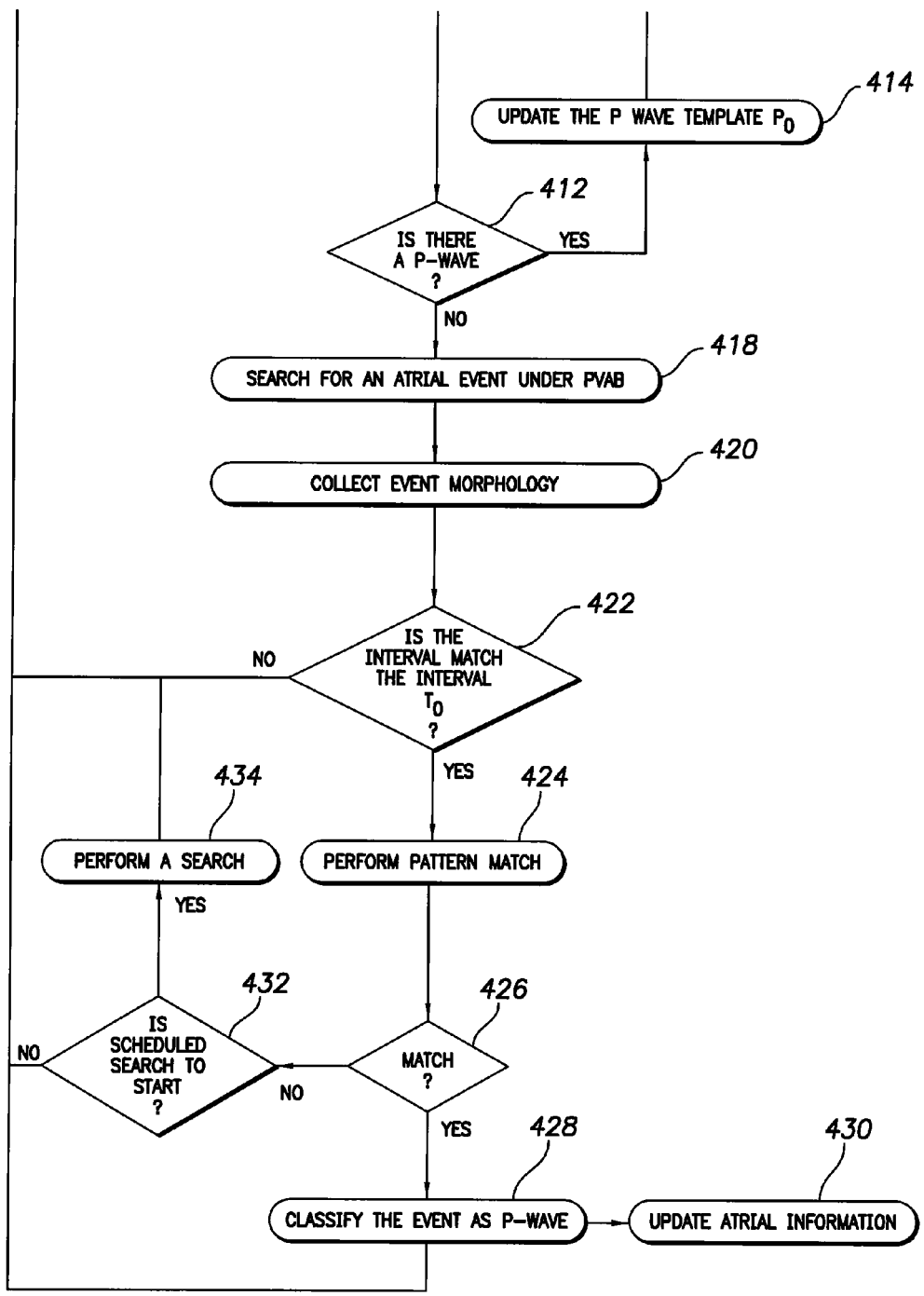

FIGS. 5-7 illustrate a more detailed example, wherein specific numerical calculations are set forth. As in the preceding example, the pacer/ICD classifies P-waves/atrial events based on the characteristics of the P-waves/atrial events, such as interval history, patterns and/or morphology. The technique exploits the fact that P-waves/atrial events originating from the sinus node or atrial tachycardia foci-sites are most likely to have a different time interval, a different pattern and a different morphology in comparison to over-sensed ventricular events. Accordingly, the pacer/ICD continuously collects and updates, beat-by-beat, a short-term P-wave interval history, sequence pattern and/or a morphology template for atrial events. When the system determines that the atrial activities are regular, i.e. the intervals between the atrial events are stable and/or the sequence pattern is consistent (e.g. uniform interval, continuous lengthening of intervals, continuous shortening of intervals or alternating patterns of intervals, etc.), then the system searches for potential atrial event(s) detected within the PVAB interval. If an atrial event found within the PVAB interval has the same interval, sequence pattern and/or morphology of predecessor atrial events, the system classifies the event as a real or true sensed P-wave/atrial-originated event, instead of an over-sensed ventricular event, and the pacer/ICD then updates atrial diagnostics accordingly, such as counting the event for atrial rate calculation.

FIG. 5 provides a high-level, schematic illustration of the exemplary procedure. During a first general step 300, the pacer/ICD passively obtains the history P-waves within the patient, as follows:
a. Continuously record and calculate an atrial event sequence pattern $S_0$
   $S_0$=such as, constant interval pattern, ascending interval, descending interval or bigeminal alternating interval.
b. Continuously record and calculate an average $T_0$ of P-P interval and its deviation $\Delta T_0$, which includes an "alert" P-wave and the P-wave during the relative refractory period for a pre-defined number ($N_0$) of events. Then, dynamically update the average for the rhythms as:
   $T_0=(T_0*(N_0-1)+\text{current P-P interval})/N_0$.
   $\Delta T_0=\text{Sqrt}(((\Delta T_0*(N_0-1))^2+(\text{current P-P interval}-T_0)^2)/\text{Sqrt}((N_0-1)^2+1)$ for uniform distributed event sequence, where $\Delta T_0$ is obtained using the standard deviation.
   $\Delta T_0=\text{Sqrt}(\Delta T^2_{even}+\Delta T^2_{odd})/\text{Sqrt}(2)$ for alternating distributed event sequence
   where $\Delta T_{even}$ is obtained using even order event.
   where $\Delta T_{odd}$ is obtained using odd order event
   $N_{odd}=N_{event}=N_0/2$
   $\Delta T_0=\text{Sqrt}(((\Delta T_0*(N_0-1))^2+(\text{current P-P interval}-T_0-\text{correction factor for ascending or descending}$ sequence)$^2$)/Sqrt(($N_0-1)^2$+1) for ascending or descending event sequence respectively c. Continuously collect the morphology of P-waves which are not under (or inside) the PVAB interval, calculate a template $P_0$ for $N_1$ events and dynamically update a template $P_0$.

During a second general step 302, the pacer/ICD predicts and detects hidden atrial events, as follows:

a. After obtaining the initial $T_0$, $S_0$, etc., predict beat-by-beat where next P-wave/atrial event will potentially occur based on $T_0$ and $S_0$, given that $\Delta T_0 <=$ a predefined threshold (to "qualify"); otherwise continue to reevaluate T, $\Delta T$, P, and S. In one particular example, the prediction from the Sequence $S_0$ and $T_0$ includes:

if Sequence is uniform, the next interval is current time+ $T_0$ if Sequence is continuous (i.e. uniform) lengthening, the next interval is current time+$T_0$+$\Delta$lengthening if Sequence is continuous (i.e. uniform) shortening, the next interval is current time+$T_0$+$\Delta$shortening if Sequence is alternating, the next interval is current time+$T_0$+$\Delta$next−alternating timing.

b. If a P-wave/atrial event is predicted to occur under PVAB interval, record the IEGM signal under the PVAB interval at the predicted timing with a defined window from the $\alpha\Delta T$, without opening sensing refractory, where $\alpha$ is a coefficient ranging from 0.5 to 3. Also, determine if the signal recorded is above the sensing threshold.

c. If the signal is above the sensing threshold, then the event is a P-wave candidate. Calculate the P-P interval from the previous P-wave to the candidate P-wave signal under the PVAB interval using IEGM/or sensing circuit. Compare the P-P interval with the predicted T. If the difference is smaller than a pre-defined threshold, the candidate P-wave is labeled as a real or true P-wave event.

d. If the difference of comparison is larger than a pre-defined threshold, the candidate event is classified as a candidate for ventricular signal, such as T-wave, over sensing.

e. Continually update the $T_0$, $\Delta T$, P, and S as new P waves are recorded.

During a third general step 304, the pacer/ICD applies morphology as an additional qualifier, as follows:

a. Morphological pattern recognition is employed to further confirm the presence of true P-wave. That is, when an event is recognized as a hidden P-wave candidate based on the interval analysis, perform a pattern match of the candidate event with the $P_0$.

b. If the template $P_0$ and candidate P-wave morphology match, then the candidate P-wave is thereby further confirmed as a real or true P-wave event.

c. If not, then the candidate P-wave is deemed to be over-sensed ventricular activity.

During a fourth general step 306, the pacer/ICD alters the pacing intervals for use as an additional qualifier, as follows:

a. If several consecutive hidden atrial events are present, vary the atrial pacing or ventricular pacing interval by 20-40 ms, so that the next predicted atrial interval will be also altered by 20-40 msec. If the detected atrial signal is atrial oversensing of the ventricles, the R-P$_{candidate}$ or V-P$_{candidate}$ interval will stay the same and P-P (T-wave over-sensing) will change. Hence, this step further distinguishes a real P-wave from the over-sensing of ventricular signal, such as T wave:

If the predicted event still remains present after record the IEGM data, the event is confirmed as part of a true atrial rhythm.

If the predicted event is no longer present in the recorded IEGM data, the event is deemed to be a ventricular event, thus, the algorithm labels this event and the previous hidden events as not being indicative of a true atrial rhythm event.

FIG. 6 illustrates the aforementioned steps in flowchart form. Briefly, at step 400, the pacer/ICD collects P-P intervals during sinus rhythm and, at step 402, calculates the accumulative average using: $T_0 = T_m + P$-P and also calculates $\Delta T$. (Note that, within steps 408 and 416, the values for $T_0$ and $T_m$ are divided by N. Alternatively, such division could instead be performed at step 402.) At step 404, the pacer/ICD collects the morphology template $P_0$. Once there are at least $N_0$ measurements, as determined at step 406, the pacer/ICD then calculates mean values for using $T_m = T_m/N$ and $\Delta T_0$ at step 408. At step 410, the value for $\Delta T_0$ is then used to qualify, i.e., initiate a hidden P-wave search based, as discussed above, on $\Delta T_0 <=$ a predefined threshold. That is, the search for hidden P-waves is only performed if $\Delta T_0$ is small, indicating that previous intervals are stable. If so, the pacer/ICD then detects the next P-wave, at step 412. If the P-wave is detected before the next PVAB interval, then the pacer/ICD updates the P-wave template $P_0$ at step 414 and updates $T_0$ based on $T_0 = (T_0*(N-1)+P$-P$)/N_0$, at step 416. If no P-wave is detected before the PVAB interval then, at step 418, the pacer/ICD searches for an atrial event under (i.e. inside) the PVAB interval and, at step 420, collects morphology on any events found therein. Thus, in this example, the device "predicts" whether a P-wave will occur within the next PVAB interval by determining whether a P-wave was first detected outside the PVAB, at step 412. If a P-wave was detected before the PVAB, then, $T_0 = T_m + P$-P and $\Delta T$ will be updated for next atrial intrinsic event. The procedure will be repeated. If, instead, a P-wave was not detected before the PVAB, then a hidden P-wave might occur within the PVAB, and so the PVAB is opened to search for the hidden P-wave. However, as can be appreciated, more sophisticated prediction procedures may be performed based, e.g. on prior P-wave patterns, etc. for the purposes of determining whether to open a given PVAB.

Assuming the latest PVAB interval has been opened and a candidate event has been found therein, then at step 422, the pacer/ICD compares the P-P interval for the candidate event against prior P-P intervals ($T_0$) to determine if there is a P-P interval-based match. (Note that the procedure of step 422 may also be regarded as a form of "prediction." That is, the device uses P-P intervals to determine the expected location of the next P-wave within the PVAB. The device then compares that predicted location to the actual location of the candidate hidden P-wave to determine if there is an interval-based match.) If there is a P-P interval-based match, the pacer/ICD then performs a pattern-based match, at step 424, i.e. the device determines whether the location of the atrial event is consistent with the pattern of prior P-waves, as discussed above. If there is a pattern-based match, at step 426, then the event is classified as a P-wave, at step 428, and atrial information, such as atrial rate, is updated at step 430.

Although not shown, processing then returns to step 412 for analysis of additional hidden P-waves. However, if there is no match at step 426, then the pacer/ICD determines, at step 432, if a scheduled search is to start. If so, a search is performed at step 434; if not processing returns to step 412. The search is performed to uncover hidden atrial activity if no P-waves have been encountered for some time. During the search of step 434, the timing of pacing events may be adjusted in an effort to vary the relative location of P-waves to aid in their detection. [Note that step 432 is only reached if no intrinsic P-waves have been found, either outside the PVAB interval (at step 412) or inside the PVAB interval (at step 426). A timer may be used at step 432 to track the duration of time since the last P-wave was found (hidden or otherwise). If the timer exceeds some predetermined threshold, the device then performs the hidden P-wave search of step 434.] FIG. 7 illustrates a pair of stored IEGMs 450 collected by a pacemaker implanted within a patient, which illustrate hidden atrial events. The two graphs include the same IEGM trace data as in the first and second graphs of FIG. 1, but include upward arrows 452 pointing to each of the P-waves the pacer/ICD detected. The intervals between P-waves are also identified in the first of the two graphs by sideways arrows 454. The average of the intervals between the P-waves is approximately 300 ms (i.e., 200 beats per minute (bpm)). Circles 456 indicate where P-waves appear under (i.e. during) the PVAB interval. In the example of FIG. 7, the device ignored the P-waves within the PVAB interval, resulting in an effective atrial interval of 600 ms (i.e., 100 bpm) leading to an unnecessary auto mode switch exit. However, a pacer/ICD equipped to perform the techniques of the invention described herein would detect the atrial events within the PVAB interval and classify those events as true P waves. Hence, the events would be counted in the atrial rate calculation to maintain the calculated atrial rate at ~200 bpm. As such, the pacer/ICD would not switch out of the non-tracking DDI mode, thus avoiding the mode switch oscillation.

The hidden atrial event detection techniques described herein can be exploited for use with a variety of cardiac signal processing techniques for use in a variety of implantable medical systems. For the sake of completeness, a detailed description of an exemplary pacer/ICD will now be provided, which can be equipped to perform the techniques described herein.

Exemplary Pacer/ICD/Lead System

FIG. 8 provides a simplified diagram of the pacer/ICD of FIG. 2, which is a dual-chamber stimulation device capable of treating both fast and slow arrhythmias with stimulation therapy, including cardioversion, defibrillation, and pacing stimulation. To provide atrial chamber pacing stimulation and sensing, pacer/ICD 10 is shown in electrical communication with a heart 512 by way of a left atrial lead 520 having an atrial tip electrode 522 and an atrial ring electrode 523 implanted in the atrial appendage. Pacer/ICD 10 is also in electrical communication with the heart by way of a right ventricular lead 530 having, in this embodiment, a ventricular tip electrode 532, a right ventricular ring electrode 534, a right ventricular (RV) coil electrode 536. Typically, the right ventricular lead 530 is transvenously inserted into the heart so as to place the RV coil electrode 536 in the right ventricular apex. Accordingly, the right ventricular lead is capable of receiving cardiac signals, and delivering stimulation in the form of pacing and shock therapy to the right ventricle.

To sense left atrial and ventricular cardiac signals and to provide left chamber pacing therapy, pacer/ICD 10 is coupled to a "coronary sinus" lead 524 designed for placement in the "coronary sinus region" via the coronary sinus os for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus. Accordingly, an exemplary coronary sinus lead 524 is designed to receive atrial and ventricular cardiac signals and to deliver left ventricular pacing therapy using at least a left ventricular tip electrode 526 and a left ventricular ring electrode 529 and to deliver left atrial pacing therapy using at least a left atrial ring electrode 527, and shocking therapy using at least an SVC coil electrode 528. With this configuration, biventricular pacing can be performed. Although only three leads are shown in FIG. 8, it should also be understood that additional stimulation leads (with one or more pacing, sensing and/or shocking electrodes) may be used in order to efficiently and effectively provide pacing stimulation to the left side of the heart or atrial cardioversion and/or defibrillation.

Figure 9:
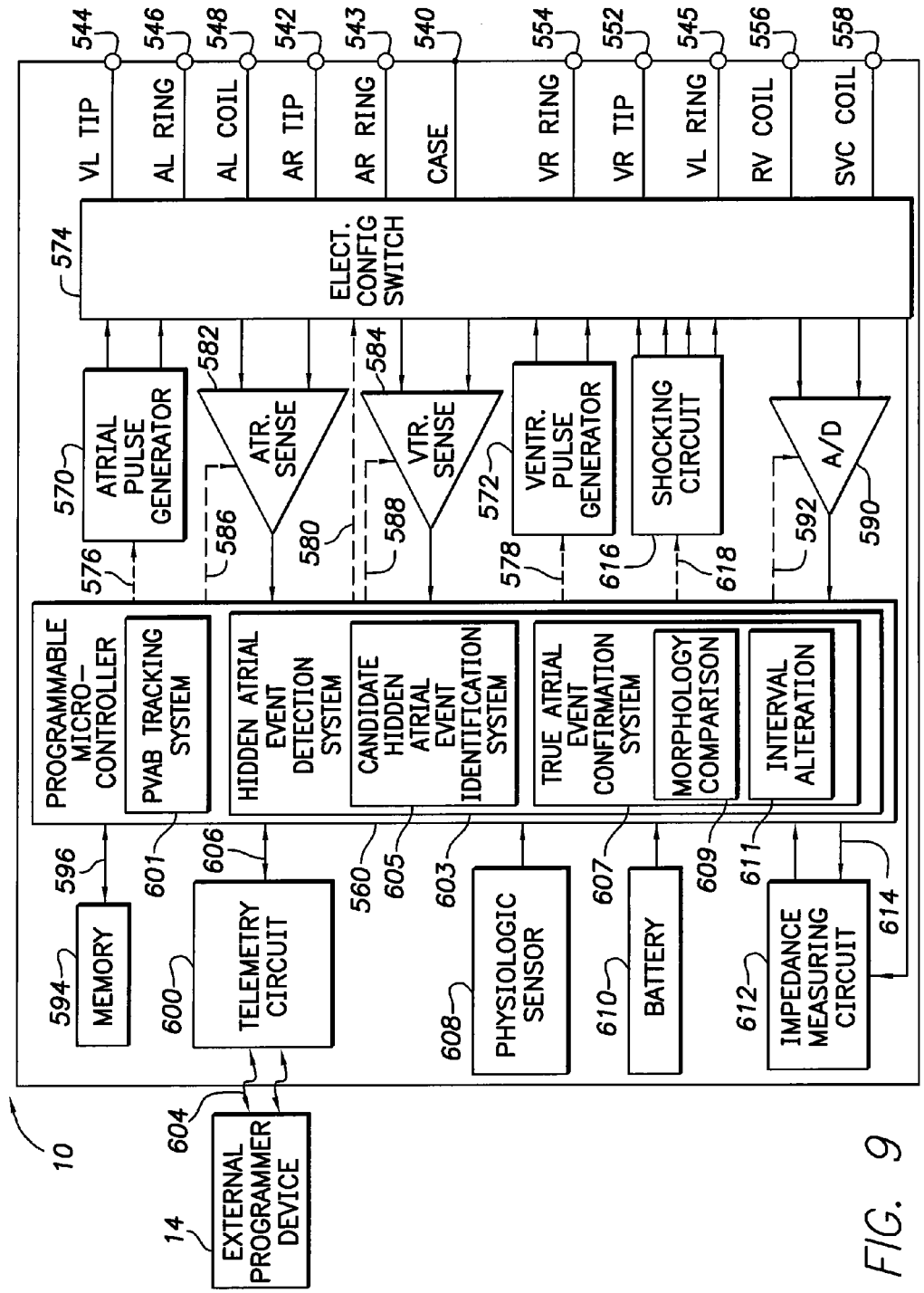
FIG. 9 is a functional block diagram of the pacer/ICD of FIG. 8, illustrating basic circuit elements that provide cardioversion, defibrillation and/or pacing stimulation in four chambers of the heart and particularly illustrating a hidden atrial arrhythmia detection system.

A simplified block diagram of internal components of pacer/ICD 10 is shown in FIG. 9. While a particular pacer/ICD is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation as well as providing for the aforementioned apnea detection and therapy.

The housing 540 for pacer/ICD 10, shown schematically in FIG. 9, is often referred to as the "can", "case" or "case electrode" and may be programmably selected to act as the return electrode for all "unipolar" modes. The housing 540 may further be used as a return electrode alone or in combination with one or more of the coil electrodes, 528, 536 and 538, for shocking purposes. The housing 540 further includes a connector (not shown) having a plurality of terminals, 542, 543, 544, 545, 546, 548, 552, 554, 556 and 558 (shown schematically and, for convenience, the names of the electrodes to which they are connected are shown next to the terminals). As such, to achieve right atrial sensing and pacing, the connector includes at least a right atrial tip terminal ($A_R$ TIP) 542 adapted for connection to the atrial tip electrode 522 and a right atrial ring ($A_R$ RING) electrode 543 adapted for connection to right atrial ring electrode 523. To achieve left chamber sensing, pacing and shocking, the connector includes at least a left ventricular tip terminal ($V_L$ TIP) 544, a left ventricular ring terminal ($V_L$ RING) 545, a left atrial ring terminal ($A_L$ RING) 546, and a left atrial shocking terminal ($A_L$ COIL) 548, which are adapted for connection to the left ventricular ring electrode 526, the left atrial tip electrode 527, and the left atrial coil electrode 528, respectively. To support right chamber sensing, pacing and shocking, the connector further includes a right ventricular tip terminal ($V_R$ TIP) 552, a right ventricular ring terminal ($V_R$ RING) 554, a right ventricular shocking terminal ($R_V$ COIL) 556, and an SVC shocking terminal (SVC COIL) 558, which are adapted for connection to the right ventricular tip electrode 532, right ventricular ring electrode 534, the RV coil electrode 536, and the SVC coil electrode 538, respectively.

At the core of pacer/ICD 10 is a programmable microcontroller 560, which controls the various modes of stimulation therapy. As is well known in the art, the microcontroller 560 (also referred to herein as a control unit) typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 560 includes the ability to process or monitor input signals (data) as controlled by a program code stored in a designated block of memory. The details of the design and operation of the microcontroller 560 are not critical to the invention. Rather, any suitable microcontroller 560 may be used that carries out the functions described herein. The use of microprocessor-based control circuits for performing timing and data analysis functions are well known in the art.

As shown in FIG. 9, an atrial pulse generator 570 and a ventricular pulse generator 572 generate pacing stimulation pulses for delivery by the right atrial lead 520, the right ventricular lead 530, and/or the coronary sinus lead 524 via an electrode configuration switch 574. It is understood that in order to provide stimulation therapy in each of the four chambers of the heart, the atrial and ventricular pulse generators, 570 and 572, may include dedicated, independent pulse generators, multiplexed pulse generators or shared pulse generators. The pulse generators, 570 and 572, are controlled by the microcontroller 560 via appropriate control signals, 576 and 578, respectively, to trigger or inhibit the stimulation pulses.

The microcontroller 560 further includes timing control circuitry (not separately shown) used to control the timing of such stimulation pulses (e.g., pacing rate, atrio-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, etc., which is well known in the art. Switch 574 includes a plurality of switches for connecting the desired electrodes to the appropriate I/O circuits, thereby providing complete electrode programmability. Accordingly, the switch 574, in response to a control signal 580 from the microcontroller 560, determines the polarity of the stimulation pulses (e.g., unipolar, bipolar, combipolar, etc.) by selectively closing the appropriate combination of switches (not shown) as is known in the art.

Atrial sensing circuits 582 and ventricular sensing circuits 584 may also be selectively coupled to the right atrial lead 520, coronary sinus lead 524, and the right ventricular lead 530, through the switch 574 for detecting the presence of cardiac activity in each of the four chambers of the heart. Accordingly, the atrial (ATR. SENSE) and ventricular (VTR. SENSE) sensing circuits, 582 and 584, may include dedicated sense amplifiers, multiplexed amplifiers or shared amplifiers. The switch 574 determines the "sensing polarity" of the cardiac signal by selectively closing the appropriate switches, as is also known in the art. In this way, the clinician may program the sensing polarity independent of the stimulation polarity. Each sensing circuit, 582 and 584, preferably employs one or more low power, precision amplifiers with programmable gain and/or automatic gain control and/or automatic sensitivity control, bandpass filtering, and a threshold detection circuit, as known in the art, to selectively sense the cardiac signal of interest. The automatic gain and/or sensitivity control enables pacer/ICD 10 to deal effectively with the difficult problem of sensing the low amplitude signal characteristics of atrial or ventricular fibrillation. The outputs of the atrial and ventricular sensing circuits, 582 and 584, are connected to the microcontroller 560 which, in turn, are able to trigger or inhibit the atrial and ventricular pulse generators, 570 and 572, respectively, in a demand fashion in response to the absence or presence of cardiac activity in the appropriate chambers of the heart.

For arrhythmia detection, pacer/ICD 10 utilizes the atrial and ventricular sensing circuits, 582 and 584, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "Fib-waves") are then classified by the microcontroller 560 by comparing them to a predefined rate zone limit (i.e., bradycardia, normal, atrial tachycardia, atrial fibrillation, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, antitachycardia pacing, cardioversion shocks or defibrillation shocks).

Cardiac signals are also applied to the inputs of an analog-to-digital (A/D) data acquisition system 590. The data acquisition system 590 is configured to acquire intracardiac electrogram signals, convert the raw analog data into a digital signal, and store the digital signals for later processing and/or telemetric transmission to an external device 602. The data acquisition system 590 is coupled to the right atrial lead 520, the coronary sinus lead 524, and the right ventricular lead 530 through the switch 574 to sample cardiac signals across any pair of desired electrodes. The microcontroller 560 is further coupled to a memory 594 by a suitable data/address bus 596, wherein the programmable operating parameters used by the microcontroller 560 are stored and modified, as required, in order to customize the operation of pacer/ICD 10 to suit the needs of a particular patient. Such operating parameters define, for example, pacing pulse amplitude or magnitude, pulse duration, electrode polarity, rate, sensitivity, automatic features, arrhythmia detection criteria, and the amplitude, waveshape and vector of each shocking pulse to be delivered to the patient's heart within each respective tier of therapy. Other pacing parameters include base rate, rest rate and circadian base rate.

Advantageously, the operating parameters of the implantable pacer/ICD 10 may be non-invasively programmed into the memory 594 through a telemetry circuit 600 in telemetric communication with an external device 602, such as a programmer, transtelephonic transceiver or a diagnostic system analyzer, or a bedside monitoring system. The telemetry circuit 600 is activated by the microcontroller by a control signal 606. The telemetry circuit 600 advantageously allows IEGMs and other electrophysiological signals and/or hemodynamic signals and status information relating to the operation of pacer/ICD 10 (as stored in the microcontroller 560 or memory 594) to be sent to the external programmer device 602 through an established communication link 604.

Pacer/ICD 10 further includes an accelerometer or other physiologic sensor 608, commonly referred to as a "rate-responsive" sensor because it is typically used to adjust pacing stimulation rate according to the exercise state of the patient. However, the physiological sensor 608 may further be used to detect changes in cardiac output, changes in the physiological condition of the heart, or diurnal changes in activity (e.g., detecting sleep and wake states) and to detect arousal from sleep. Accordingly, the microcontroller 560 responds by adjusting the various pacing parameters (such as rate, AV Delay, V-V Delay, etc.) at which the atrial and ventricular pulse generators, 570 and 572, generate stimulation pulses. While shown as being included within pacer/ICD 10, it is to be understood that the physiologic sensor 608 may also be external to pacer/ICD 10, yet still be implanted within or carried by the patient. A common type of rate responsive sensor is an activity sensor incorporating an accelerometer or a piezoelectric crystal, which is mounted within the housing 540 of pacer/ICD 10. Other types of physiologic sensors are also known, for example, sensors that sense the oxygen content of blood, respiration rate and/or minute ventilation, pH of blood, ventricular gradient, etc.

The pacer/ICD additionally includes a battery 610, which provides operating power to all of the circuits shown in FIG. 9. The battery 610 may vary depending on the capabilities of pacer/ICD 10. If the system only provides low voltage therapy, a lithium iodine or lithium copper fluoride cell may be utilized. For pacer/ICD 10, which employs shocking therapy, the battery 610 must be capable of operating at low current drains for long periods, and then be capable of providing high-current pulses (for capacitor charging) when the patient requires a shock pulse. The battery 610 should also have a predictable discharge characteristic so that elective replacement time can be detected. Accordingly, pacer/ICD 10 is preferably capable of high voltage therapy and appropriate batteries.

As further shown in FIG. 9, pacer/ICD 10 is shown as having an impedance measuring circuit 612 which is enabled by the microcontroller 560 via a control signal 614. Various uses for an impedance measuring circuit include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring respiration; and detecting the opening of heart valves, measuring lead resistance, etc. The impedance measuring circuit 120 is advantageously coupled to the switch 64 so that any desired electrode may be used.

In the case where pacer/ICD 10 is intended to operate as an implantable cardioverter/defibrillator (ICD) device, it detects the occurrence of an arrhythmia, and automatically applies an appropriate electrical shock therapy to the heart aimed at terminating the detected arrhythmia. To this end, the microcontroller 560 further controls a shocking circuit 616 by way of a control signal 618. The shocking circuit 616 generates shocking pulses of low (up to 0.5 joules), moderate (0.5-11 joules) or high energy (11 to at least 40 joules), as controlled by the microcontroller 560. Such shocking pulses are applied to the heart of the patient through at least two shocking electrodes, and as shown in this embodiment, selected from the left atrial coil electrode 528, the RV coil electrode 536, and/or the SVC coil electrode 538. The housing 540 may act as an active electrode in combination with the RV electrode 536, or as part of a split electrical vector using the SVC coil electrode 538 or the left atrial coil electrode 528 (i.e., using the RV electrode as a common electrode). Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 11-40 joules), delivered asynchronously (since R-waves may be too disorganized), and pertaining exclusively to the treatment of fibrillation. Accordingly, the microcontroller 560 is capable of controlling the synchronous or asynchronous delivery of the shocking pulses.

Insofar as hidden atrial events and arrhythmias are concerned, microcontroller 560 includes various components equipped or programmed to perform the operations discussed above. Briefly, the microcontroller includes a PVAB interval tracking system 601 operative to track a post-ventricular event interval (such as a PVAB interval) within electrical cardiac signals sensed by the device. A hidden atrial event detection system 603 detects atrial arrhythmias that might otherwise be obscured by the PVAB interval. Detection system 603 includes a candidate hidden atrial event identification system 605 operative to identify a candidate atrial event within the signals occurring during the PVAB interval using techniques discussed above, such as by exploiting ongoing atrial event patterns to predict the location of the P-wave. Detection system 603 also includes a true atrial event determination system 607 operative to determine whether candidate atrial events found within PVAB intervals are true atrial events based on a comparison of characteristics of the candidate atrial event and characteristics of prior atrial events within the patient. To this end, determination system 607 includes a morphology comparison system 609 (for comparing the morphology of the candidate P-wave against the morphology of prior P-waves within the patient) and an interval alteration system 611 (for altering atrial or ventricular pacing intervals to test whether candidate atrial events are true atrial events. Additional components may be provided as well.

Note that not all of the microcontroller components shown need be installed within any given pacer/ICD. Also, depending upon the implementation, the various components of the microcontroller may be implemented as separate software modules or the modules may be combined to permit a single module to perform multiple functions. In addition, although shown as being components of the microcontroller, some or all of these components may be implemented separately from the microcontroller, using application specific integrated circuits (ASICs) or the like.

What have been described are various exemplary techniques performed by an implantable cardiac stimulation device for detecting hidden cardiac events to improve the operation of AMS and for improving the detection of atrial tachycardias. Modifications can be made thereto without departing from the scope of the invention. Note also that the term "including" as used herein is intended to be inclusive, i.e. "including but not limited to."

What is claimed is:

1. In an implantable cardiac stimulation device, a method comprising:
    obtaining characteristics of true atrial events during normal sinus rhythm including one or more of true atrial event intervals, true atrial event patterns and true atrial event morphology; and
    subsequently detecting for true atrial events during a post-ventricular atrial blanking (PVAB) interval as follows:
        predicting whether a true atrial event is expected to occur during the PVAB interval based on one or more of the previously obtained characteristics of true atrial events;
        if a true atrial event is expected to occur during the PVAB, then examining an atrial sensing channel signal during the PVAB interval to identify any electrical events therein exceeding a predetermined sensing threshold, each of said identified events being designated a candidate atrial event; and
        for each candidate atrial event, determining whether the candidate atrial event is a true atrial event by comparing characteristics of the candidate atrial event and the previously obtained characteristics of true atrial events.

2. The method of claim 1 wherein the post-ventricular atrial blanking (PVAB) interval is activated on an atrial sensing channel following one or more of a ventricular depolarization event and a ventricular pacing pulse.

3. The method of claim 2 further comprising updating an atrial rate calculation based on any true atrial events detected within the PVAB interval.

4. The method of claim 3 further comprising controlling device operations based, at least in part, on the updated atrial rate.

5. The method of claim 4 wherein the device is capable of automatically switching between a tracking mode and a non-tracking mode and wherein such mode switching is performed based on the updated atrial rate.

6. The method of claim 1 wherein the true atrial event patterns include one or more predetermined patterns including: uniform intervals, lengthening intervals, shortening intervals, and alternating intervals.

7. The method of claim 1 wherein determining whether the candidate atrial event is a true atrial event comprises:
    predicting the timing of a next atrial event based on true atrial event patterns and true atrial event intervals; and determining whether an electrical event occurs during the PVAB interval with the predicting timing and, if so, identifying the event as a true atrial event.

8. The method of claim 7 further comprising confirming the true atrial event based on true atrial event morphology by comparing the morphology of the atrial event to the morphology of true atrial events.

9. The method of claim 7 further comprising confirming the true atrial event based on an alteration in pacing intervals.

10. The method of claim 9 wherein confirming the true atrial event based on an alteration in pacing intervals comprises:
changing a pacing interval so that the predicted timing for the next atrial event likewise changes; and
determining whether an electrical event occurs with the new predicting timing and, if so, confirming the event as a true atrial event.

11. The method of claim 1 wherein determining whether the candidate atrial event is a true atrial event comprises:
comparing a measured interval from a last true atrial event to the candidate atrial event to a previous interval between true atrial events;
if the measured interval matches the previous interval, comparing a detected morphological parameter of the candidate atrial event to a corresponding morphological parameter of a true atrial event; and
if the detected morphological parameter matches the corresponding morphological parameter of a true atrial event, concluding the candidate atrial event is a true atrial event.

12. The method of claim 1 wherein determining whether the candidate atrial event is a true atrial event comprises:
comparing a measured interval from a last true atrial event to the candidate atrial event to a previous interval between true atrial events;
if the measured interval matches the previous interval, comparing a detected morphological parameter of the candidate atrial event to a corresponding morphological parameter of a true atrial event; and
if the detected morphological parameter matches the corresponding morphological parameter of a true atrial event, varying a pacing interval by an adjusted amount, identifying a subsequent candidate atrial event within the signals sensed by the atrial sensing channel occurring during the post-ventricular event interval, determining whether the timing of the subsequent candidate atrial event corresponds to the adjusted amount; and
if the timing of the subsequent candidate atrial event corresponds to the adjusted amount, concluding the candidate atrial event is a true atrial event.

13. In an implantable cardiac stimulation device, a system comprising:
a controller operative to obtain characteristics of true atrial events during normal sinus rhythm including one or more of true atrial event intervals, true atrial event patterns and true atrial event morphology;
a candidate atrial event identification system operative to predict whether a true atrial event is expected to occur during a post-ventricular atrial blanking (PVAB) interval based on one or more of the previously obtained characteristics of true atrial events; and if a true atrial event is expected to occur during the PVAB, then examine an atrial sensing channel signal during the PVAB interval to identify any electrical events therein exceeding a predetermined sensing threshold, each of said identified events being designated a candidate atrial event; and
a true atrial event determination system operative to determine, for each candidate atrial event, whether the candidate atrial event is a true atrial event based on a comparison of characteristics of the candidate atrial event and the previously obtained characteristics of true atrial events.

14. In an implantable cardiac stimulation device capable of tracking a post-ventricular event interval within electrical cardiac signals sensed by an atrial sensing channel of the device following certain ventricular events, a system comprising:
means for obtaining characteristics of true atrial events during normal sinus rhythm including one or more of true atrial event intervals, true atrial event patterns and true atrial event morphology;
means for predicting whether a true atrial event is expected to occur during a post-ventricular atrial blanking (PVAB) interval based on one or more of the previously obtained characteristics of true atrial events; and if a true atrial event is expected to occur during the PVAB, then examining an atrial sensing channel signal during the PVAB interval to identify any electrical events therein exceeding a predetermined sensing threshold, each of said identified events being designated a candidate atrial event; and
means for determining, for each candidate atrial event, whether the candidate atrial event is a true atrial event based on a comparison of characteristics of the candidate atrial event and the previously obtained characteristics of true atrial events.

15. In an implantable cardiac stimulation device capable of automatically switching between a tracking mode and a non-tracking mode, a method comprising the steps of:
obtaining characteristics of true atrial events during normal sinus rhythm including one or more of true atrial event intervals, true atrial event patterns and true atrial event morphology; and
subsequently detecting for true atrial events during a post-ventricular atrial blanking (PVAB) interval as follows:
predicting whether a true atrial event is expected to occur during the PVAB interval based on one or more of the previously obtained characteristics of true atrial events;
if a true atrial event is expected to occur during the PVAB, then examining an atrial sensing channel signal during the PVAB interval to identify any electrical events therein exceeding a predetermined sensing threshold, each of said identified events being designated a candidate atrial event; and
determining whether the newly detected events are true atrial events based on a comparison of characteristics of the candidate atrial event and the previously obtained characteristics of true atrial events within the patient;
determining an atrial rate based on true atrial events; and
switching modes in response to changes in the atrial rate.

* * * * *